United States Patent [19]

Tung et al.

[11] Patent Number: 4,994,604

[45] Date of Patent: Feb. 19, 1991

[54] FORMATION AND RESOLUTION OF IBUPROFEN LYSINATE

[75] Inventors: Hsien-Hsin Tung, Scotch Plains; Stanley Waterson, Colonia; Scott D. Reynolds, Plainsboro, all of N.J.

[73] Assignee: Merck & Co., Inc., Rahway, N.J.

[21] Appl. No.: 463,198

[22] Filed: Jan. 10, 1990

[51] Int. Cl.$^5$ ............................................. C07B 57/00
[52] U.S. Cl. .................................... 562/401; 562/402; 562/496
[58] Field of Search .......................... 562/401, 402, 496

[56] References Cited

PUBLICATIONS

S. Yamada et al, *J. Org. Chem.* 38, 4408, pp. 1058–1062, (1973).
S. Yamada et al, *J. Org. Chem.* 40, 3360, pp. 1062–1065, (1975).

*Primary Examiner*—Werren B. Lone
*Assistant Examiner*—Vera C. Clarke
*Attorney, Agent, or Firm*—Melvin Winokur; Joseph F. DiPrima

[57] ABSTRACT

A process is disclosed for the formation and resolution of (S)-ibuprofen-(S)-lysine. The process employs preferential crystallization to separate a pair of diasteromeric salts, (S)-ibuprofen-(S)-lysine and (R)-ibuprofen-(S)-lysine.

8 Claims, No Drawings

FORMATION AND RESOLUTION OF IBUPROFEN LYSINATE

BACKGROUND OF THE INVENTION

Pharmacological properties are often dependent on a particular stereochemistry and thus the resolution of a racemic mixture is a useful chemical process.

Ibuprofen, a well know analgesic, is a racemic mixture of carboxylic acids of formula (I):

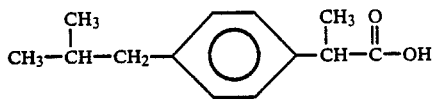

However, although ibuprofen is marketed as the racemic mixture, the (S)-enantiomer is known to be the active agent. If (S)-ibuprofen is to be sold commercially there exists a need for an efficient preferential resolution of racemic ibuprofen. Furthermore it would be desirable for the resolution process to lead directly to an amino acid salt of (S)-ibuprofen since such salts are more soluble and thus may offer pharmaceutical advantages over the carboxylic acid.

There are two classical routes to the resolution of racemic mixtures such as (R)(S)-ibuprofen.

The first requires finding a chiral amine which, when reacted with the (R)(S)-ibuprofen, will form diastereomeric salts the solubilities of which are so different from each other that the diastereomers may be separated, one from the other, by simple crystallization.

The above procedure has two disadvantages: chiral amines, such as (S)-alpha-methylbenzylamine, are expensive reagents, and the product of the separation is not (S)-ibuprofen, but its amine salt. Thus the separation process must be supplemented with procedures to free the (S)-ibuprofen from its amine salt, recover the chiral amine, and, if desired, convert the (S)-ibuprofen to a preferred salt such as an amino acid salt.

The second classical resolution route is preferential crystallization. However, (R)(S)-ibuprofen as such cannot be resolved by preferential crystallization, or any other crystallization technique, because as a crystalline material it takes the form of a racemic compound rather than a mixture of crystals of (R)-ibuprofen and crystals of (S)-ibuprofen. Thus, to use preferential crystallization requires finding a derivative of ibuprofen which does not crystallize in the form of a racemic compound. Non-chiral amines, such as tert-butylamine and diethylamine are suitable for this purpose. However, except for amine costs, preferential crystallization via these amine salts shares the disadvantages cited for the chiral amine route described above.

DETAILED DESCRIPTION OF THE INVENTION

The present invention is a process for the formation and resolution of (S)-ibuprofen-(S)-lysine, which comprises:

(a) contacting (R)(S)-ibuprofen and (S)-lysine in an aqueous-organic solvent mixture;

(b) separating any suspended solid from the mixture;

(c) cooling the clear mixture until the mixture is supersaturated with respect to each of the (S)-ibuprofen-(S)-lysine and (R)-ibuprofen-(S)-lysine salts;

(d) contacting the supersaturated mixture with a slurry of (S)-ibuprofen-(S)-lysine in an aqueous-organic solvent;

(e) separating the formed crystalline (S)-ibuprofen-(S)-lysine.

Racemic ibuprofen is mixed with an organic solvent which is miscible with water. Illustrating such solvents are ethanol, methanol, isopropanol and acetone. The (S)-lysine is mixed with water, and the ibuprofen and lysine solutions are combined.

The mixture is agitated for a time period sufficient to crystallize all the salts, if any, in excess of the solubility limit. The suspended salts are separated to obtain a clear mother liquor which is generally saturated with respect to the diastereomeric salts (S)-ibuprofen-(S)-lysine and (R)-ibuprofen-(S)-lysine. Filtration may be employed to effect the separation. The liquor is then cooled to a temperature at which it is supersaturated with respect to each of the diastereomeric salts. It is preferred that the liquor be cooled to the point at which maximum supersaturation is obtained with respect to each salt without nucleation of either crystallizable species. Typically the temperature of the mother liquor must be lowered by about 5° C. to reach maximum supersaturation without precipitation of either salt. However, the degree of cooling will depend on the particular solvent composition. The supersaturated liquor is then passed into a vessel containing a slurry of (S)-ibuprofen-(S)-lysine, hereafter referred to as the (S,S)-salt, in the same solvent system employed above for the mixture of racemic ibuprofen and (S)-lysine. In the presence of the (S,S) salt crystals acting as a seed, the supersaturation of the (S,S)-salt in the feed liquor is released by the growth of further crystals of the (S,S)-salt. Conversely there is little or no change in the (R)-ibuprofen-(S)-lysine (hereafter referred to as the (R,S)-salt) supersaturation because the growth rate of the (R,S) crystals is essentially zero in the absence of any initial (R,S) salt seed. The (S,S) crystals are then separated and washed with aqueous-organic solvent to yield (S)-ibuprofen-(S)-lysine of purity ≧ 98%. Separation may be accomplished by filtration or centrifugation.

The above described process can be employed on a batch or a continuous basis. In the continuous procedure the mother liquor obtained after the separation of (S,S) crystals is placed back into step (a) to reform a mixture of the diastereomeric salts.

The above process is an implementation of the principle of preferential crystallization a process which takes advantage of the fact that the growth rate of crystals is a function not only of the solution supersaturation, which provides the driving force for crystal growth, but also of the amount of seed crystal surface available for growth. By providing a large amount of (S,S) salt seed crystal surface, and essentially no (R,S) salt seed crystal surface, an environment is created in which (S,S) salt crystals grow at a substantial rate, and (R,S) salt crystals at a negligible rate. The practical application of preferential crystallization was possible in the present invention due to Applicants' surprising findings that ibuprofen lysine can tolerate a high degree of supersaturation in solution without crystal growth and that (S)-ibuprofen-(S)-lysine and (R)-ibuprofen-(S)-lysine form a mixture and not a compound.

The present process can be successfully accomplished over a range of temperatures at the salt formation step (a) and the supersaturation step (c). The only restriction is that the temperature in step (c) not cause spontaneous nucleation of either crystallizable species. Typically, salt formation in Step (a) is accomplished at about 30° C. and with ethanol/H₂O (97/3 v/v) as the solvent mixture and supersaturation is achieved with about a 5° C. cooling, to about 25° C.

The present invention can be operated across a range of organic solvent to water ratios. Higher water concentrations increase the solubilities of the two salts. With ethanol/water mixtures, water concentrations above 5% V/V lead to the crystallization of the (S,S) salt in the form of its monohydrate; the anhydrous form is obtained from lower water concentration. Preferably the percentage water by volume is less than 15%. Illustrative ratios of ethanol/water are 97/3 and 92/8 v/v.

Although the above description cites only (S)-lysine as the salt forming agent for the resolution, (R)-lysine could be used with similar effect. In this case (R)-ibuprofen-(R)-lysine would be employed in the seeding stage and high purity crystalline (R)-ibuprofen-(R)-lysine would be obtained.

Racemic ibuprofen and (S)-lysine and (R)-lysine are all commercially available.

The following example illustrates the process of the present invention and as such is not to be considered as limiting the invention set forth in the claims appended hereto:

EXAMPLE 1

Preparation and Resolution of (S)-Ibuprofen-(S)-Lysine 167 grams of racemic ibuprofen and 118 grams of (S)-lysine were charged into 180 cc of water and 5.82 liters of ethanol were added. The resulting slurry was agitated and aged at 30° C. for 24 hours. A clear liquor was drawn off through a filter and the liquor cooled to 25° C. The resulting supersaturated liquor was then added to a slurry of 50 grams of 99.4% (S)-ibuprofen-(S)-lysine. The precipitated solid was separated by filtration and the mother liquor recycled to the slurry mixture of racemic ibuprofen and (S)-lysine. The procedure was continued until essentially all the (S)-ibuprofen in the original charge was depleted. This procedure resulted in the formation of 144 grams of 98.1–98.8% pure (S)-ibuprofen-(S)-lysine.

EXAMPLE 2

Preparation and Resolution of (S)-Ibuprofen-(S)-Lysine 1. 2.0 kg racemic ibuprofen and 1.6 kg S-lysine monohydrate were combined with 18 to 20 liters of EtOH/Water 97/3 V/V solvent mixture. The solution was charged to a feed tank which contained about 20 to 30 gallons seed bed of (R)-ibuprofen-(S)-lysine and (S)-ibuprofen-(S)-lysine with a slurry concentration of about 150 liter.

2. A slurry of about 10 liters was transferred from the feed tank to an empty dissolver.

3. The dissolver temperature was adjusted to about 31° C.

4. The slurry in the dissolver was filtered and the filtrate sent to the crystallizer at a rate of 600 ml/min. and the retentate returned to the dissolver.

5. The crystallizer contained about 30 liter seed bed of (S)-ibuprofen-(S)-lysine with a slurry concentration of about 150 gram/liter and a crystallizer temperature of about 23° C.

6. The slurry in the crystallizer was filtered and the filtrate sent back to the dissolver at a rate such that the liquid level in the crystallizer remained constant while the retentate was returned to the crystallizer.

7. After about 6 to 7 hours continuous operation of steps 3 to 6, all the (S)-ibuprofen-(S)-lysine in the dissolver was depleted. About 4 liters crystallizer slurry was harvested and filtered. The cake contained about 600 grams (S)-ibuprofen-(S)-lysine with an optical purity of about 99%.

8. 4 liters of dissolver filtrate was sent to the crystallizer to maintain the liquid level in the crystallizer.

9. About 6 liters of dissolver slurry which contained mainly the (R)-ibuprofen-(S)-lysine was transferred to a container.

12. Steps 2 to 9 were repeated.

What is claimed is:

1. A process for the formation and resolution of (S)-ibuprofen-(S)-lysine which comprises:
    (a) contacting (R)(S)-ibuprofen and (S)-lysine in an aqueous-organic solvent mixture;
    (b) separating any suspended solid from the mixture;
    (c) cooling the clear mixture until the mixture is supersaturated with respect to each of the (S,S) and (R,S) salts;
    (d) contacting the supersaturated mixture with a slurry of (S)-ibuprofen-(S)-lysine in an aqueous-organic solvent;
    (e) separating the formed crystalline (S)-ibuprofen-(S)-lysine.

2. A process of claim 1 wherein the aqueous-organic solvent is selected from the group consisting of: water/ethanol, water/methanol, water/isopropanol, and water/acetone.

3. A process of claim 2 wherein the aqueous/organic solvent is water/ethanol.

4. A process of claim 3 wherein the volume percent of water is less than 15 percent.

5. A process of claim 4 wherein the volume percent of water is 8 percent or less.

6. A process of claim 5 wherein the volume percent of water is 3 percent or less.

7. A process of claim 6 wherein the Step (c) cooling is about 5° C.

8. A process for the resolution of (S)-ibuprofen-(S)-lysine which comprises:
    (i) contacting a mixture supersaturated in (S)-ibuprofen-(S)-lysine and (R)-ibuprofen-(S)-lysine in an aqueous-organic solvent with a slurry of (S)-ibuprofen-(S)-lysine in an aqueous-organic solvent;
    (ii) separating the formed crystalline (S)-ibuprofen-(S)-lysine.

* * * * *